(12) United States Patent
Udupa et al.

(10) Patent No.: US 10,739,433 B2
(45) Date of Patent: Aug. 11, 2020

(54) CALIBRATING BODY IMPEDANCE MEASUREMENT SYSTEMS

(71) Applicant: TEXAS INSTRUMENTS INCORPORATED, Dallas, TX (US)

(72) Inventors: Anand Hariraj Udupa, Bangalore (IN); Hussam Ahmed, Calicut (IN); Jagannathan Venkataraman, Bangalore (IN); Sandeep Kesrimal Oswal, Bangalore (IN); Prabin Krishna Yadav, Bangalore (IN); Anand Reghunathan, Bangalore (IN); Kiran Rajmohan, Ernakulam (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 573 days.

(21) Appl. No.: 15/465,484

(22) Filed: Mar. 21, 2017

(65) Prior Publication Data
US 2017/0265771 A1 Sep. 21, 2017

(30) Foreign Application Priority Data
Mar. 21, 2016 (IN) .............................. 201641009865

(51) Int. Cl.
*G01R 35/00* (2006.01)
*A61B 5/00* (2006.01)
(Continued)

(52) U.S. Cl.
CPC .......... *G01R 35/005* (2013.01); *A61B 5/0537* (2013.01); *A61B 5/7225* (2013.01);
(Continued)

(58) Field of Classification Search
CPC ..... A61B 5/0537; A61B 5/7225; A61B 5/053; A61B 2560/0223; G01R 35/005; G01R 27/02; G01R 27/16
See application file for complete search history.

(56) References Cited

U.S. PATENT DOCUMENTS 3,851,641 A 12/1974 Toole et al.
3,871,359 A 3/1975 Pacela
(Continued)

OTHER PUBLICATIONS

AFE4300, Low-Cost, Integrated Analog Front-End for Weight-Scale and Body Composition Measurement, available at http://www.ti.com/lit/ds/symlink/afe4300.pdf, Jun. 2013 (30 pages).
(Continued)

*Primary Examiner* — Sean P Dougherty
(74) *Attorney, Agent, or Firm* — Brian D. Graham; Charles A. Brill; Frank D. Cimino

(57) ABSTRACT

A system may comprise: an excitation current source; a first electrode coupled to the excitation current source; and a second electrode coupled to the excitation current source. The first and second electrodes may be configured to pass an excitation current from the excitation current source through a human body. First and second calibration resistors may be coupled to and positioned between the excitation current source and the first electrode. Third and fourth calibration resistors may be coupled to and positioned between the excitation current source and the second electrode. The system may also comprise a sensor configured to measure voltages across each of the first, second, third, and fourth calibration resistors.

16 Claims, 7 Drawing Sheets

(51) Int. Cl.
*A61B 5/053* (2006.01)
*G01R 27/02* (2006.01)
*G01R 27/16* (2006.01)

(52) U.S. Cl.
CPC .............. *G01R 27/02* (2013.01); *A61B 5/053* (2013.01); *A61B 2560/0223* (2013.01); *G01R 27/16* (2013.01)

(56) References Cited

U.S. PATENT DOCUMENTS

| | | | |
|---|---|---|---|
| 4,459,995 A | | 7/1984 | Conners et al. |
| 4,708,146 A | * | 11/1987 | Lane ................... A61B 5/0809 324/709 |
| 5,121,064 A | * | 6/1992 | Eller ................... G01R 35/005 324/601 |
| 5,187,096 A | | 2/1993 | Giaever et al. |
| 6,050,267 A | * | 4/2000 | Nardella .............. A61B 5/0536 128/899 |
| RE37,954 E | * | 1/2003 | Sato ................... A61B 5/0537 600/547 |
| 7,385,443 B1 | * | 6/2008 | Denison ................... H03F 3/38 330/10 |
| 7,443,175 B2 | | 10/2008 | Podhajsky et al. |
| 7,941,210 B2 | | 5/2011 | Matthiessen et al. |
| 2001/0001680 A1 | | 5/2001 | Farmer et al. |
| 2002/0079910 A1 | | 6/2002 | Fukuda |
| 2004/0127811 A1 | * | 7/2004 | Higuchi ............... A61B 5/0537 600/547 |
| 2004/0152996 A1 | * | 8/2004 | Gersing ................. A61B 5/053 600/547 |
| 2007/0043303 A1 | * | 2/2007 | Osypka ................ A61B 5/7228 600/547 |
| 2007/0244410 A1 | * | 10/2007 | Fridman ............ A61B 5/04001 600/554 |
| 2008/0012582 A1 | | 1/2008 | Jang et al. |
| 2008/0036475 A1 | | 2/2008 | Waki |
| 2008/0275361 A1 | | 11/2008 | Loriga et al. |
| 2009/0076336 A1 | * | 3/2009 | Mazar ................... A61B 5/0402 600/300 |
| 2009/0264792 A1 | * | 10/2009 | Mazar ................... A61B 5/0531 600/547 |
| 2010/0004548 A1 | | 1/2010 | Rytky |
| 2010/0100003 A1 | * | 4/2010 | Chetham ............. A61B 5/0537 600/547 |
| 2010/0102834 A1 | | 4/2010 | Shyu |
| 2010/0168530 A1 | * | 7/2010 | Chetham ............. A61B 5/0537 600/301 |
| 2010/0327887 A1 | * | 12/2010 | Denison ............... A61B 5/0002 324/692 |
| 2011/0169511 A1 | | 7/2011 | Nordin et al. |
| 2011/0313311 A1 | * | 12/2011 | Gaw ...................... A61B 5/053 600/547 |
| 2012/0143034 A1 | * | 6/2012 | Gaw ................... A61B 5/0416 600/393 |
| 2012/0172747 A1 | * | 7/2012 | Fukuda ................ A61B 5/0537 600/547 |
| 2014/0088394 A1 | * | 3/2014 | Sunderland .......... A61B 5/0408 600/373 |
| 2015/0293045 A1 | | 10/2015 | Udupa et al. |
| 2015/0305648 A1 | | 10/2015 | Udupa et al. |
| 2016/0006448 A1 | * | 1/2016 | Melanson ........... H03M 1/0665 341/155 |
| 2017/0265771 A1 | * | 9/2017 | Udupa ................. A61B 5/0537 |

OTHER PUBLICATIONS

AFE4300 Development Guide, User's Guide, available at http://www.ti.com/lit/ug/2bau201.pdf, Aug. 2012 (46 pages).

* cited by examiner

US 10,739,433 B2

CALIBRATING BODY IMPEDANCE MEASUREMENT SYSTEMS

CROSS-REFERENCE TO RELATED APPLICATIONS

This application claims priority to Indian Provisional App. No. 201641009865, which was filed on Mar. 21, 2016 and is incorporated herein by reference.

BACKGROUND

Various devices are commonly used to measure the impedance of the human body. Body impedance measurements, in turn, may be used to determine information such as body composition (e.g., the percentage of the body that is composed of fat or water). Such devices typically contain an excitation current source, electrodes to apply the excitation current through the body, and sensing equipment to measure the voltage across the electrodes. The voltage may then be used to determine body impedance. These devices may require periodic calibration to maintain the accuracy of body impedance measurements.

SUMMARY

At least some embodiments are directed to a system that may comprise an excitation current source; a first electrode coupled to the excitation current source; and a second electrode coupled to the excitation current source. The first and second electrodes may be configured to pass an excitation current from the excitation current source through a human body. First and second calibration resistors may be coupled to and positioned between the excitation current source and the first electrode. Third and fourth calibration resistors may be coupled to and positioned between the excitation current source and the second electrode. The system may also comprise a sensor configured to measure voltages across each of the first, second, third, and fourth calibration resistors. One or more such embodiments may be supplemented using one or more of the following concepts, in any order and in any combination: wherein the first and second calibration resistors are coupled in series with each other; wherein the third and fourth calibration resistors are coupled in series with each other; wherein the first calibration resistor has an impedance that is within ±15% of an impedance of the third calibration resistor; wherein the second calibration resistor has an impedance that is within ±15% of an impedance of the fourth calibration resistor; further comprising a processor coupled to the sensor and configured to determine a first average of voltages measured across the first and third calibration resistors and further configured to determine a second average of voltages measured across the second and fourth calibration resistors; wherein the processor is configured to: divide a difference between the first and second averages by a difference between impedances of the first and second calibration resistors to determine an excitation current; subtract a product of the excitation current and an impedance of the first calibration resistor from the first average to produce a voltage offset; measure a body voltage across between the first and second electrodes when the first and second electrodes contact the human body; and divide a difference between the body voltage and the voltage offset by the excitation current to produce a body impedance of the human body; wherein the sensor is configured to: measure, at a time T after measurement of the voltages across the first, second, third, and fourth calibration resistors, a body voltage across the first and second electrodes when the first and second electrodes are applied to the human body; and re-measure the voltages across the first, second, third, and fourth calibration resistors after the time T has elapsed after measurement of the body voltage; further comprising a processor coupled to the sensor and configured to determine a first average of the measured and re-measured voltages across the first and third calibration resistors and further configured to determine a second average of the measured and re-measured voltages across the second and fourth calibration resistors; wherein the processor is configured to calibrate the system based on the first and second averages.

At least some embodiments are directed to a system, comprising: an excitation current source; a first electrode coupled to the excitation current source and associated with a first skin-electrode contact impedance; and a second electrode coupled to the excitation current source and associated with a second skin-electrode contact impedance. The first and second electrodes may be configured to pass an excitation current from the excitation current source through a human body. The system also may include a first calibration resistor coupled to and positioned between the excitation current source and the first electrode; a second calibration resistor coupled to the second electrode; a third calibration resistor positioned between the second calibration resistor and the excitation current source; and a sensor configured to sense voltages across each of the first, second, and third calibration resistors. The system may also comprise a processor coupled to the sensor and configured to receive the sensed voltages. The processor may be further configured to divide a difference in voltages across the second and third calibration resistors by a difference in impedances of the second and third calibration resistors to determine an excitation current. The processor may be further configured to subtract a product of the excitation current and an impedance of the third calibration resistor from the voltage across the third calibration resistor to determine a voltage offset. The processor may further be configured to measure a body voltage across two points on the human body. The processor may further be configured to divide a difference between the body voltage and the voltage offset by the excitation current to determine a body impedance. The processor may still further be configured to determine first and second skin-electrode contact impedances associated with the first and second electrodes when the first and second electrodes contact the human body. The processor may also be configured to determine an impedance variation value based on a difference between the voltages across the first and second calibration resistors and based on a total impedance between the first and second electrodes when the first and second electrodes contact the human body. The processor also may determine a corrected body impedance based on the body impedance, the first and second skin-electrode contact impedances, and the impedance variation value. Some such embodiments may be supplemented using one or more of the following concepts, in any order and in any combination: wherein the total impedance comprises the body impedance and the first and second skin-electrode contact impedances; wherein the processor is configured to determine the corrected body impedance based on a product of the body impedance and a sum, the sum being of 1 and a combination of the impedance variation value and the first and second skin-electrode contact impedances; wherein the combination comprises a product of the impedance variation value and the second skin-electrode contact impedance divided by a sum of the first and second skin-electrode contact impedances; further comprising a plurality of switches configured to reverse a direction of alternating current (AC) flowing through the first, second, and third calibration resistors, wherein the corrected body impedance accounts for parameters measured during both current flow directions; further comprising a multiplexer coupled between the processor and the first and second calibration resistors.

At least some embodiments are directed to a method, comprising: passing an excitation current from an excitation current source, through first and second calibration resistors, through a human body, through third and fourth calibration resistors, and back to the excitation current source; determining a first voltage across the first calibration resistor, a second voltage across the second calibration resistor, a third voltage across the third calibration resistor, and a fourth voltage across the fourth calibration resistor; averaging the first and third voltages to produce a first average; averaging the second and fourth voltages to produce a second average; and performing a calibration using the first and second averages. Such embodiments may be supplemented using one or more of the following concepts, in any order and in any combination: further comprising: determining the excitation current by dividing a difference of the first and second averages by a difference between impedances of the first and second calibration resistors; calculating a voltage offset by subtracting a product of the excitation current and the impedance of the first calibration resistor from the first average; measuring a body voltage across two points on the human body; and calculating a body impedance of the human body by dividing a difference between the body voltage and the voltage offset by the excitation current; further comprising measuring, at a time T after determining the first, second, third, and fourth voltages, a body impedance in the human body, and re-determining the first, second, third, and fourth voltages after the time T has elapsed after measurement of the body impedance; further comprising: averaging determined first and third voltages to produce a first average; averaging determined second and fourth voltages to produce a second average; calculating a body impedance of the human body based in part on the first and second averages.

BRIEF DESCRIPTION OF THE DRAWINGS

For a detailed description of various examples, reference will now be made to the accompanying drawings in which.

DETAILED DESCRIPTION

At least some embodiments in this disclosure are directed to body impedance measurement systems with calibration capabilities that are improved relative to other body impedance measurement systems. In particular, this disclosure describes various body impedance measurement circuits that are configured to self-calibrate using multiple calibration resistors (as opposed to single calibration resistor systems). The multiple calibration resistors are implemented in specific locations in the circuits that take advantage of the circuits' architectural symmetry, current flow patterns, switching configurations, and other electrical properties to facilitate more accurate calibration than other systems may achieve. These circuits and methods describing their operation are now disclosed with regard to FIGS. 1A-3B.

Figure 1A:
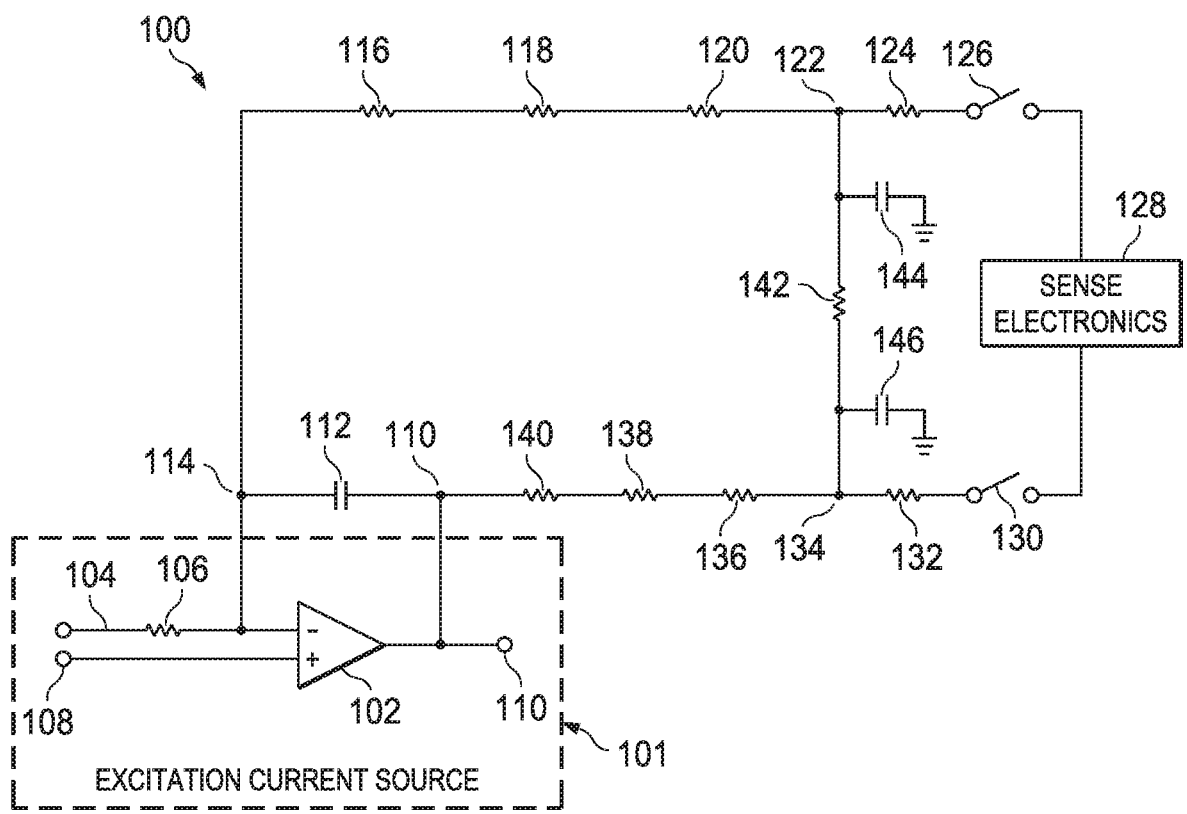
FIG. 1A is a circuit schematic diagram of an illustrative body impedance measurement and calibration system (BIMCS).

FIG. 1A is a circuit schematic diagram of an illustrative body impedance measurement and calibration system (BIMCS) 100. The circuitry depicted in FIG. 1A may, in some embodiments, constitute only part of the BIMCS 100. The BIMCS 100 may comprise an excitation current source 101 including an amplifier 102 (e.g., op-amp); an inverting input 104 that receives an excitation voltage for conversion to an excitation current; a resistor 106 (e.g., 20 kOhms); a non-inverting input 108; and an output 110. The scope of disclosure is not limited to the precise configuration depicted in FIG. 1A. The excitation current source 101 is configured to produce an excitation current that flows through the remainder of the BIMCS 100 or at least a portion of the remainder of the BIMCS 100. The gain of the amplifier 102 may be of any suitable, desired level, depending on the implementation and specifications of the various components of the BIMCS 100.

The BIMCS 100 may further comprise a shunt capacitor 112 (e.g., 47 pico-Farads) positioned between the nodes 114 and 110. Further, the BIMCS 100 may include a calibration resistor 116; a calibration resistor 118; a calibration resistor 138; and a calibration resistor 140. The impedance values of these calibration resistors may generally be chosen as desired and as may be appropriate; however, in at least some embodiments, the impedances of the calibration resistors 116 and 140 are identical or one of the impedances is within 15% of the other impedance, and in some such embodiments, the impedances of the calibration resistors 118 and 138 are identical or one of these two impedances is within 15% of the other of these two impedances. In some embodiments, the impedance values of the calibration resistors 116 and 138 are identical or one of the impedances is within 15% of the other impedance, and in some such embodiments, the impedances of the calibration resistors 118 and 140 are identical or one of these two impedances is within 15% of the other of these two impedances. Other impedance variations may be used. For instance, any calibration resistor may have an impedance that is within 20%, 25%, or more of another calibration resistor. (Although the term "impedance" is used throughout this disclosure, it should be construed broadly enough to encompass the concept of resistance as well.) Further, in some embodiments, the impedances of the calibration resistors 116 and 140 may be chosen so that they are near the low end of the expected range of values for the impedance of the human body that may be measured using the BIMCS 100 and the impedances of the calibration resistors 118 and 138 may be chosen so that they are near the high end of this range. Conversely, in some embodiments, the impedances of the calibration resistors 116 and 140 may be chosen so that they are near the high end of this expected range and the impedances of the calibration resistors 118 and 138 may be selected so that they are near the low end of this expected range. All such variations fall within the scope of this disclosure.

The BIMCS 100 may further comprise electrodes 122 and 134. These electrodes may, for instance, be electrodes that are applied to human skin to complete a circuit in the BIMCS 100. The BIMCS 100 may comprise a body impedance 142, which is the impedance of the human body to which the electrodes 122 and 134 are applied. (Use of the BIMCS 100 is not strictly limited to humans; applications with other organisms are contemplated.) This disclosure treats the body impedance 142 as part of the BIMCS 100; however, the BIMCS 100 may be considered to include fewer than all components depicted in FIG. 1A. For example, the BIMCS 100 may exclude the body impedance 142 such that the body impedance 142 is considered to be external to the BIMCS 100.

The electrode 122 is associated with an impedance when it makes contact with a body, and this impedance is depicted in FIG. 1A as a skin-electrode contact impedance 120. Similarly, the electrode 134 is associated with an impedance when it makes contact with a body, and this impedance is depicted in FIG. 1A as a skin-electrode contact impedance 136. The skin-electrode contact impedances 120 and 136 are not standalone components; instead, they are the impedances that are inherently present when the electrodes 122 and 134 contact a body. The BIMCS 100 may include parasitic capacitances 144 and 146 that appear when the electrodes 122 and 134 make contact with a body. As with the body impedance 142, the parasitic capacitances 144 and 146 may be considered external to the BIMCS 100 and thus not part of the BIMCS 100, although the scope of disclosure is not limited as such.

The components of the BIMCS 100 thus far described form an excitation circuit. The remainder of the components of the BIMCS 100 form a sense circuit. The sense circuit of the BIMCS 100 may include sense electronics 128; switches 126 and 130 configured to selectively couple the sense electronics 128 to the excitation circuit; and skin-electrode contact impedances 124 and 132 associated with electrodes 122 and 134, respectively. The sense electronics 128 are configured to sense voltages present across the electrodes 122 and 134 and to relay those measurements to a processor subsystem, such as the illustrative subsystem depicted in FIG. 1B. In some embodiments, the switches 126 and 130 may be transistors (e.g., bipolar junction transistors (BJTs)), although any type of switching mechanism may be used. The switches 126 and 130 may be controlled, for instance, by the processor subsystem 195 depicted in FIG. 1B (connections to the processor subsystem not expressly shown). Briefly referring to FIG. 1B, the processor subsystem 195 may be implemented in conjunction with any BIMCS system, whether expressly disclosed herein or not. The processor subsystem 195 may comprise a processor 196 that couples to storage 197 (e.g., random access memory, read only memory), which, in turn, stores executable code 198. The processor 196 executes the executable code 198, which causes the processor 196 to perform the actions attributed herein to the processor 196 and/or the processor subsystem 195. The processor 196 may issue control signals to various switches in BIMCSs, and it may exchange signals with the sense electronics in BIMCSs. The processor 196 may display images or other data on a display 199.

Figure 1B:
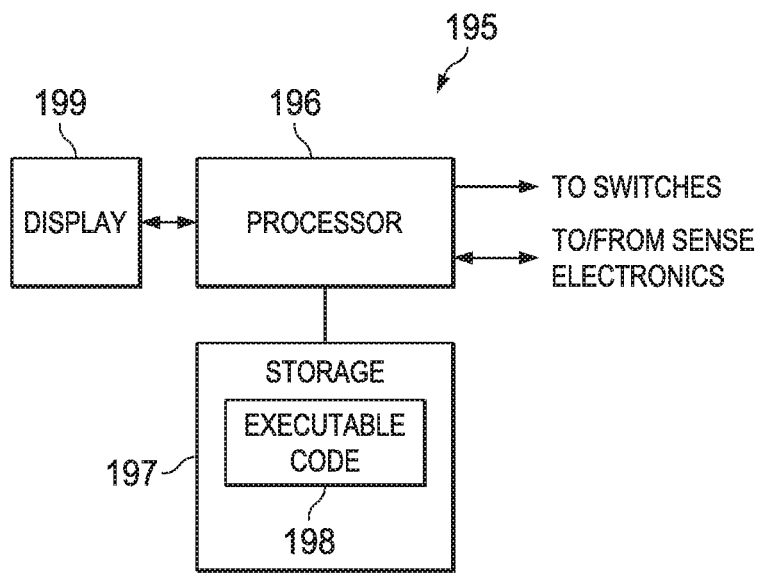
FIG. 1B is a block diagram of an illustrative processor subsystem.
Figure 1C:
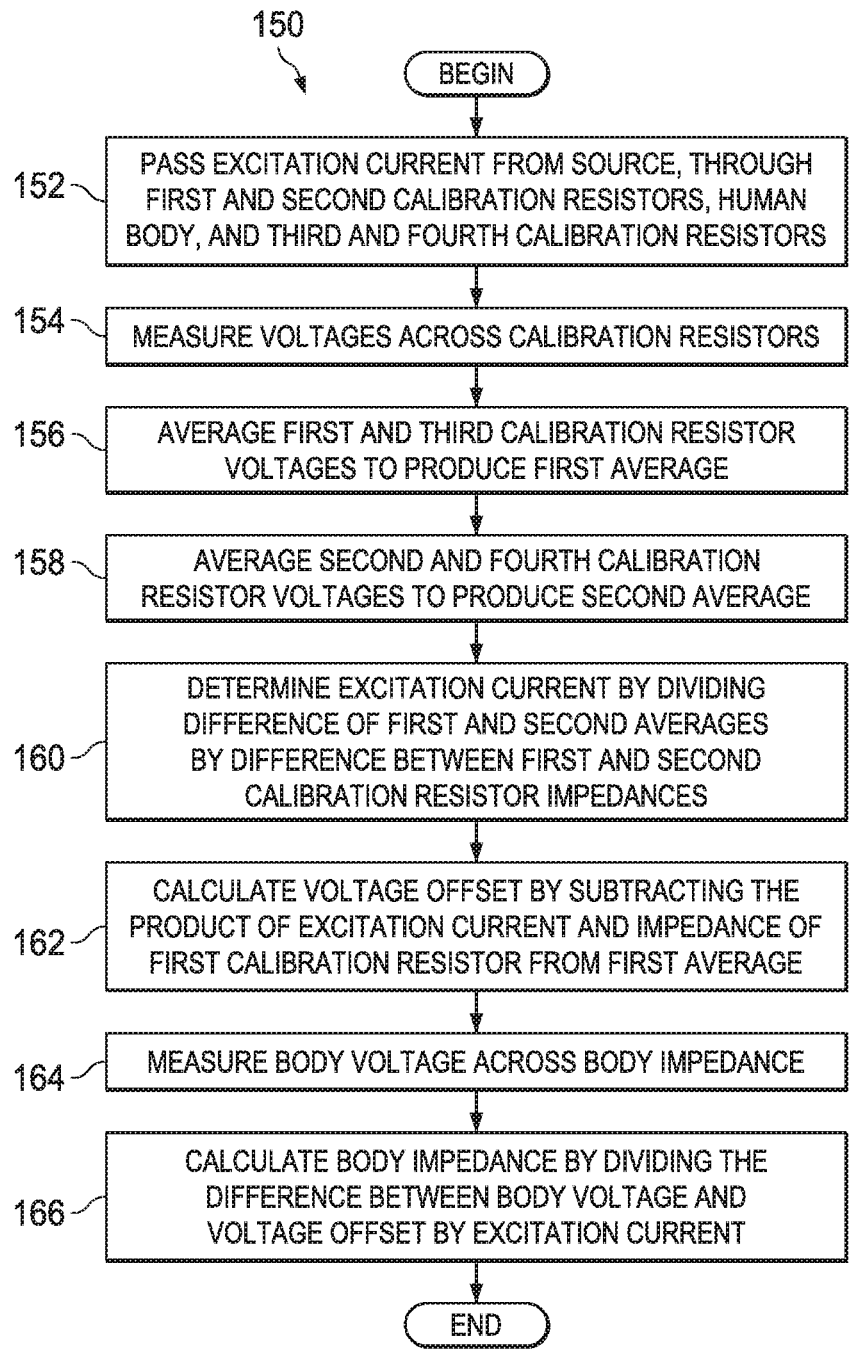
FIG. 1C is a flow diagram of an illustrative method for calibrating the illustrative BIMCS of FIG. 1A.

The operation of the BIMCS 100 is now described with respect to the flow diagram of illustrative method 150, shown in FIG. 1C. The method 150 may begin by passing an excitation current from an excitation current source through first and second calibration resistors, through a body (e.g., a human body, but any animal body may be used instead), through third and fourth calibration resistors, and back to the excitation current source (step 152). For example, briefly referring to FIG. 1A, the excitation current source 101 may generate an excitation current. When the electrodes 122 and 134 are applied to a conductive pathway (e.g., a human body), a circuit is formed and the excitation current generated by the excitation current source 101 may flow through the calibration resistors 116 and 118, the body impedance 142, and the calibration resistors 138 and 140 (the direction of current flow may vary). Excitation currents may comprise alternating current (AC) or direct current (DC).

The method 150 may further comprise measuring the voltages across the calibration resistors, with excitation currents repeatedly passed through the circuit as necessary (step 154). Referring to FIG. 1A, this step may be performed by the sense electronics 128 measuring the voltages across the calibration resistors 116, 118, 138, and 140. The sense electronics 128 may, in some embodiments, have one or more pairs of leads (not expressly shown) that couple across each of the calibration resistors to measure the voltages across the resistors. For example, the sense electronics 128 may have leads that couple between resistors 116 and 118 and between resistors 118 and electrode 122 so that it may measure the voltage across the calibration resistor 118. The sense electronics 128 may provide these voltage measurements across the calibration resistors to a processor, such as the processor 196 in FIG. 1B, and the processor may use the measured voltages, the known calibration resistor impedances, and Ohm's law to determine the excitation currents flowing through the calibration resistors 116, 118, 138, and 140. In at least some embodiments, each of the leads between a calibration resistor and the sense electronics 128 has one or more switches to electrically couple/de-couple that calibration resistor and the sense electronics 128.

The method 150 may then comprise averaging the first and third calibration resistor voltages to produce a first average (step 156). The processor 196 (FIG. 1B) may perform this step. The "first" calibration resistor may be either of the resistors 116 and 118. If the "first" calibration resistor is the resistor 116, the "third" calibration resistor may be the resistor 140. Similarly, if the "first" calibration resistor is the resistor 118, the "third" calibration resistor may be the resistor 138. The "first" calibration resistor also may be either of the resistors 140 and 138. If the "first" calibration resistor is the resistor 140, the "third" calibration resistor may be the resistor 116, and if the "first" calibration resistor is the resistor 138, the "third" calibration resistor may be the resistor 118. The method 150 may next include averaging the second and fourth calibration resistor voltages to produce a second average (step 158). The processor 196 may perform this step. The "second" calibration resistor may be either of the resistors 116 and 118. If the "second" calibration resistor is the resistor 116, the "fourth" calibration resistor may be the resistor 140. If the "second" calibration resistor is the resistor 118, the "fourth" calibration resistor may be the resistor 138. If, however, the "second" calibration resistor is the resistor 140, the "fourth" calibration resistor may be the resistor 116, and if the "second" calibration resistor is the resistor 138, the "fourth" calibration resistor may be the resistor 118.

The method 150 may then include determining an excitation current by dividing the difference between the first and second averages by the difference between the first and second calibration resistor impedances (step 160):

$$\text{Excitation current} = \frac{\text{First average} - \text{second average}}{\text{First calibration resistor impedance} - \text{Second calibration resistor impedance}} \quad (1)$$

The method 150 subsequently comprises calculating a voltage offset by subtracting the product of the excitation current and the impedance of the first calibration resistor from the first average (step 162):

$$\text{Voltage offset} = \text{First average} - \text{Excitation current} * \text{First calibration resistor impedance} \quad (2)$$

The method 150 next includes measuring the body voltage across the body impedance (e.g., body impedance 142) (step 164) and calculating the body impedance by dividing the difference between the body voltage and the voltage offset by the excitation current (step 166):

$$\text{Body Impedance} = \frac{\text{Body voltage} - \text{Voltage offset}}{\text{Excitation current}} \quad (3)$$

The body impedance may then be used as desired.

Figure 1D:
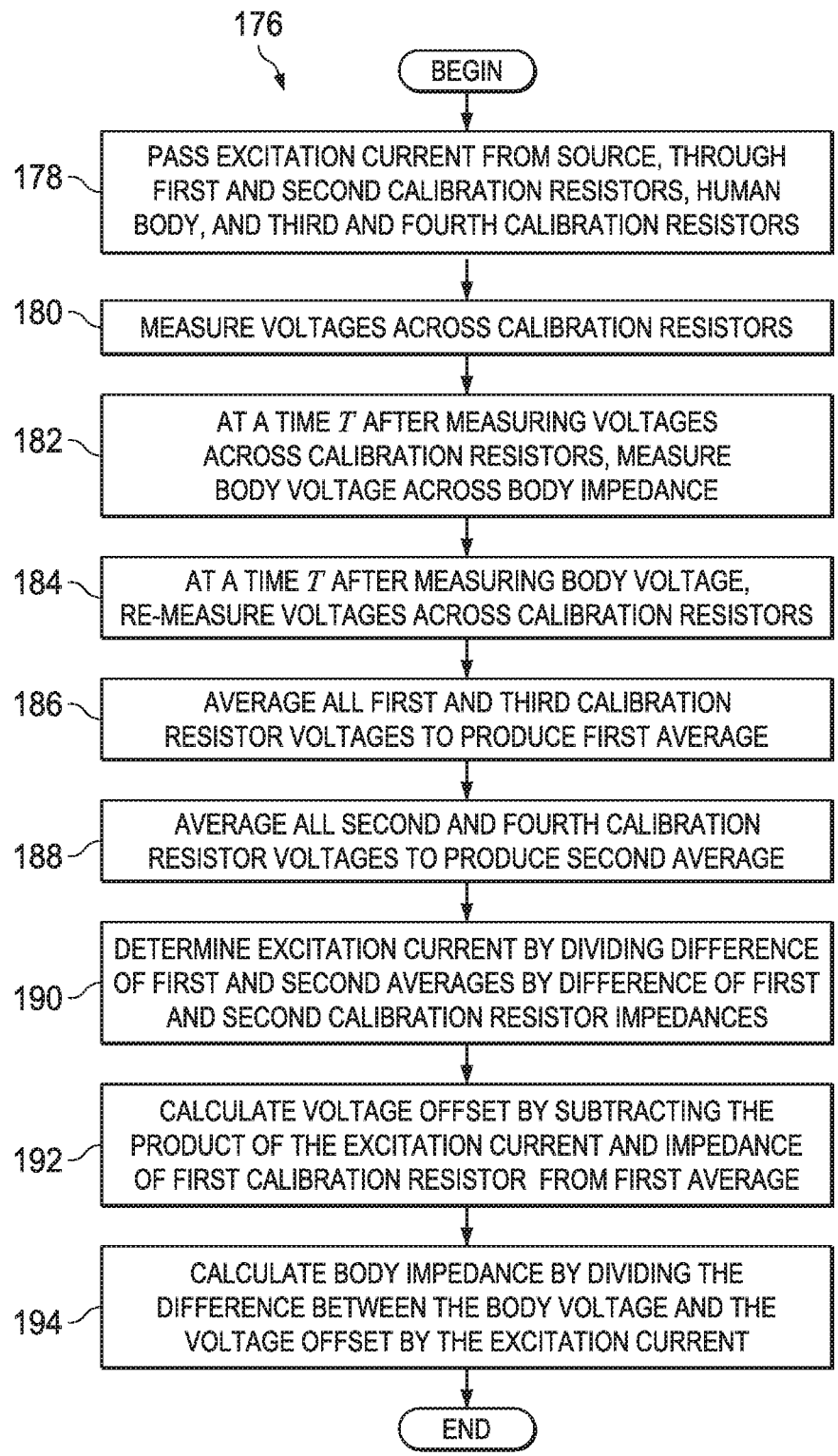
FIG. 1D is a flow diagram of another illustrative method for calibrating the illustrative BIMCS of FIG. 1A.

FIG. 1D is a flow diagram of another illustrative method 176 for calibrating the illustrative BIMCS of FIG. 1A. The method 176 is similar to the method 150, but the method 176 entails measuring calibration resistor voltages both before a body voltage measurement and after the body voltage measurement. Specifically, the calibration resistor voltages are measured at a time T before the body voltage is measured, and the calibration resistor voltages are again measured at a time T after the body voltage is measured. By averaging the calibration resistor voltages, the calibration resistor voltage values at the time the body voltage is measured may be determined with greater accuracy. The method 176 may begin by passing excitation current from the excitation current source, through first and second calibration resistors, the body, and third and fourth calibration resistors (step 178). This step is similar to step 152 in FIG. 1C and thus is not described in detail again. The method 176 may next comprise determining voltages across the calibration resistors (step 180). The processor 196 may perform this step, and because the step 180 is similar to the step 154, it is not described in further detail here.

The method 176 may further include again passing the excitation current through the circuit and determining the body voltage across the body impedance at a time T after the calibration resistor voltages are measured (step 182). If the calibration resistor voltages were measured simultaneously in step 180, the time T may be measured from that simultaneous measurement. If the calibration resistor voltages were measured sequentially in step 180, the time T may be measured from the time of the final calibration resistor voltage measurement. The method 176 may further comprise again passing excitation currents through the circuit and re-determining the impedance voltages across the calibration resistors at a time T after the step 182 (step 184). If the measurements in step 184 are performed simultaneously, the time T after step 182 may be measured up to the simultaneous measurement of step 184. If the measurements in step 184 are sequential, the time T after step 182 may be measured up to the first measurement of the step 184. The processor 196 may perform these steps. All measurements of first and third calibration resistor voltages may then be averaged to produce a first average (step 186), for example, by the processor 196. For instance, if the first and third calibration resistors are the resistors 116 and 140 in FIG. 1A, respectively, then all voltage measurements in steps 180 and 184 for the calibration resistors 116 and 140 may be averaged to produce a first average. The method 176 may then include averaging all measurements of the second and fourth calibration resistor voltages to produce a second average (step 188). The method 176 may subsequently include determining an excitation current by dividing the difference of the first and second averages by the difference of the first and second calibration resistor impedances (step 190), as expressed in (1) above. The method 176 may further comprise calculating a voltage offset by subtracting the product of the excitation current and the impedance of the first calibration resistor from the first average (step 192), as expressed in (2) above. The method 176 also comprises calculating body impedance by dividing the difference between the body voltage and the voltage offset by the excitation current (step 194), as expressed in (3) above. The body impedance may then be used as desired.

Some or all steps of the methods 150 and 176 may be performed by the processor 196, possibly in tandem with the sense electronics 128. In addition, the methods 150 and 176 may be adjusted as desired. For instance, steps may be added, deleted, modified, or rearranged as desired and as may be appropriate.

Figure 2A:
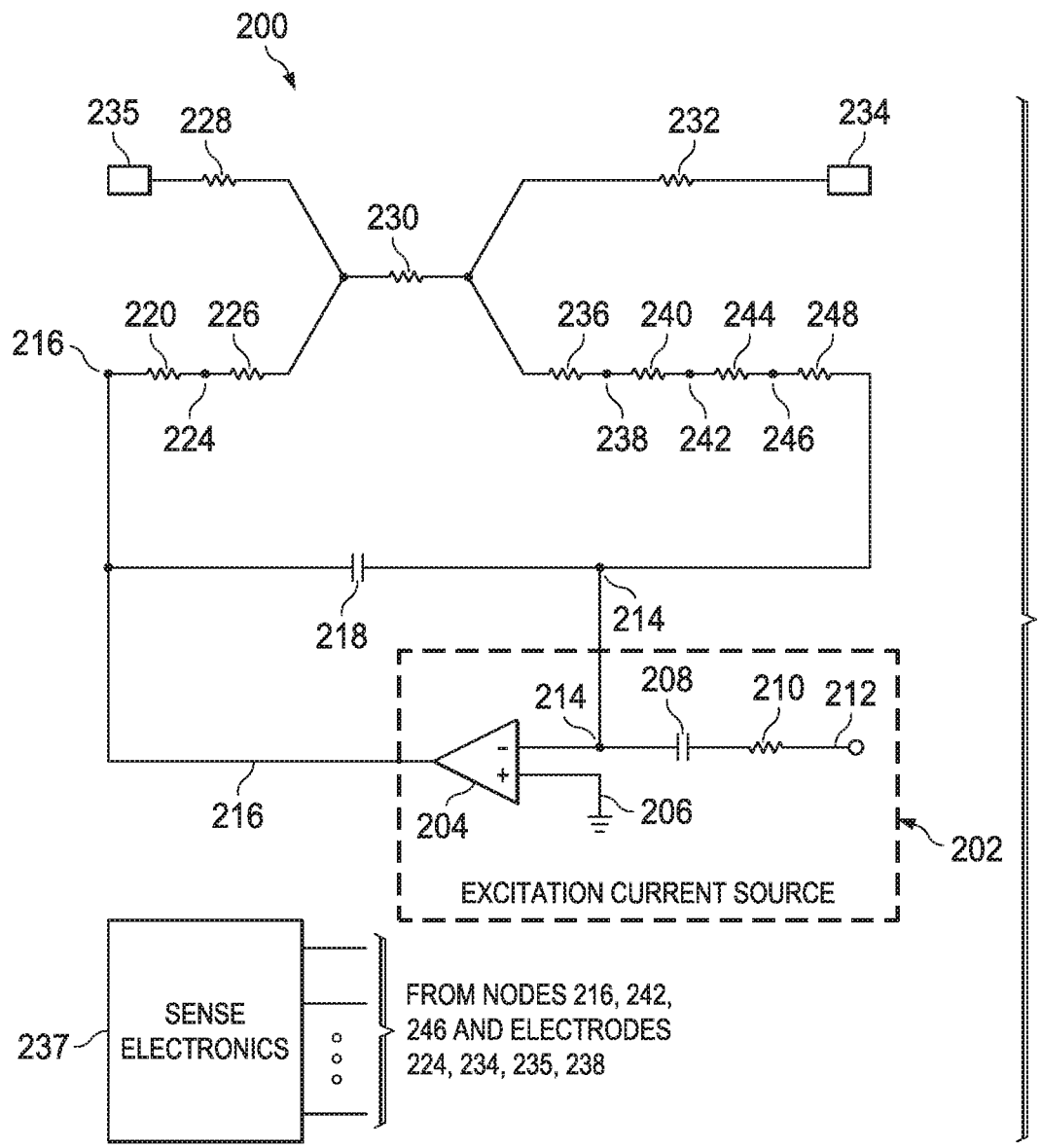
FIG. 2A is a circuit schematic diagram of another illustrative BIMCS.

FIG. 2A is a circuit schematic diagram of another illustrative BIMCS 200. The BIMCS 200 may comprise an excitation current source 202, which includes an amplifier 204 (e.g., an op-amp) with a non-inverting input 206 coupled to ground and an inverting input 214 coupled to both a capacitor 208 (e.g., 1 micro-Farad) and a resistor 210 (e.g., 20 kOhm) that couples to an input node 212. The input node 212 receives an excitation voltage and the amplifier 204 converts the excitation voltage to an excitation current. The output 216 of the amplifier 204 may couple to a calibration resistor 220. The calibration resistor 220 may couple to a skin-electrode contact impedance 226 via electrode 224. Electrode 238 may couple to calibration resistor 240, which may couple to calibration resistor 244 via node 242. The impedances of the calibration resistors 220 and 240 may be identical or one of them may be within 15% of the other. Calibration resistor 244 may couple to a shield resistor 248 (e.g., 1 kOhm) via node 246. The shield resistor 248 may protect the body from excessively high current levels and thus acts as a shield. The shield resistor 248 may couple to the input 214. A shunt capacitor 218 (e.g., 47 pico-Farads) may be positioned between the amplifier input 214 and output 216. The resistor 230 may be a body impedance (e.g., of a human body) when the electrodes 224 and 238 are applied to a body. The electrodes 224 and 238 may be associated with skin-electrode contact impedances 226 and 236, respectively, which are inherent to the electrodes upon contact with a body and are not standalone components. The sense electronics 237 may couple to the nodes 216, 242, and/or 246, and/or to electrodes 224, 238, 234, and 235, to measure voltages between any two nodes and/or electrodes. The electrodes 234 and 235 may have skin-electrode contact impedances 232 and 228 associated therewith, respectively. Sense electronics 237 may comprise a multiplexer (not expressly depicted) that facilitates the selection of any two connections to the aforementioned nodes and electrodes in the BIMCS 200 to measure voltages therebetween. The multiplexer may be controlled by, e.g., the processor 196 (FIG. 1B).

Figure 2B:
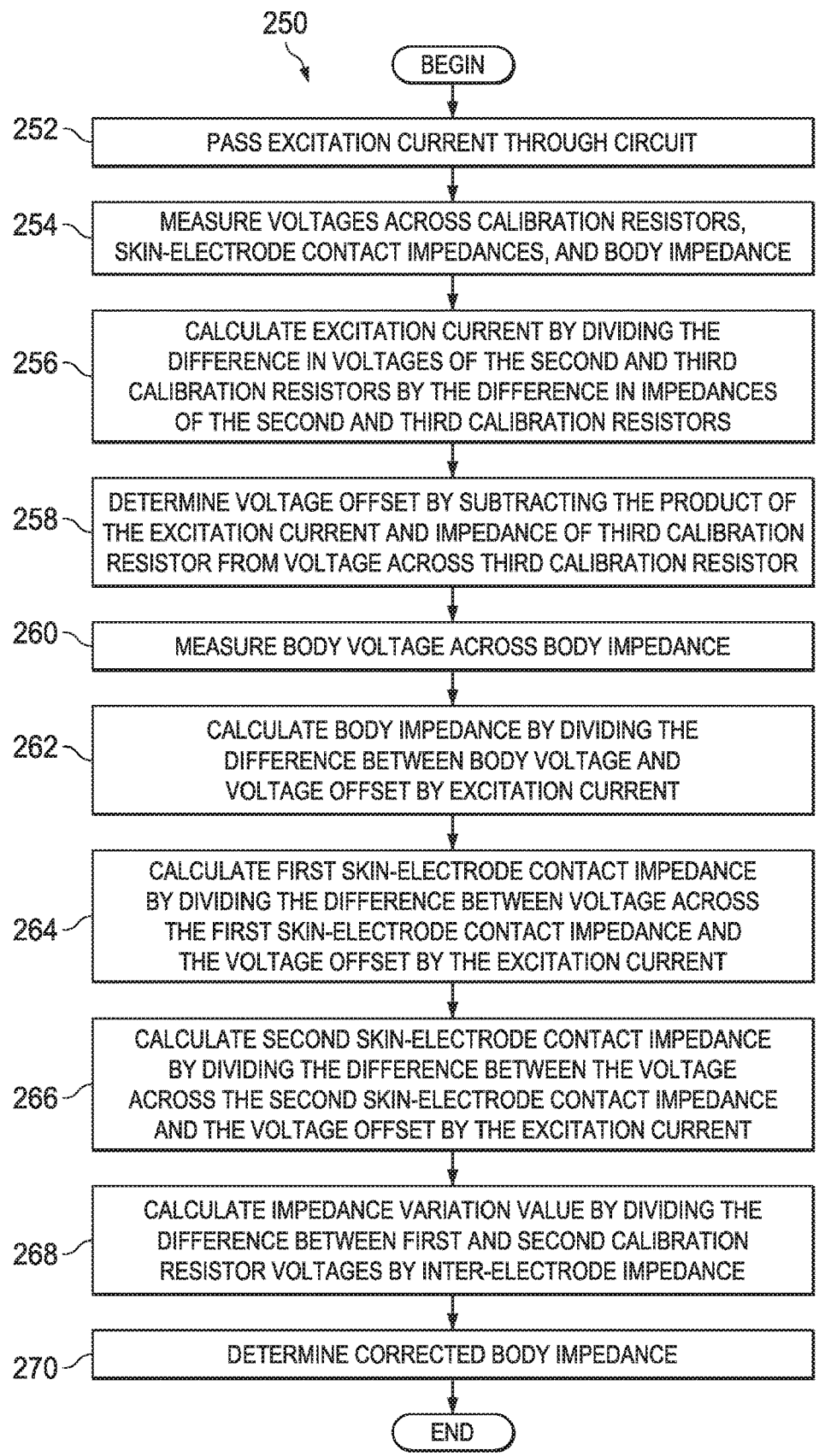
FIG. 2B is a flow diagram of an illustrative method for calibrating the illustrative BIMCS of FIG. 2A.

FIG. 2B is a flow diagram of an illustrative method 250 for calibrating the illustrative BIMCS of FIG. 2A. The steps of the method 250 may be performed in part or in entirety by the processor 196 (FIG. 1B). The method 250 may begin by passing an excitation current through the BIMCS 200

(step 252). The excitation current source 202 may provide the excitation current to the BIMCS 200. The method 250 may next comprise measuring voltages across the calibration resistors (e.g., resistors 220, 240, and 244), skin-electrode contact impedances (e.g., impedances 226 and 236), and body impedance (e.g., impedance 230) (step 254). The method may comprise calculating an excitation current by dividing the difference in voltages across the second and third calibration resistors by the difference in impedances of the second and third calibration resistors (step 256):

$$\text{Excitation current} = \frac{\text{Third calibration resistor voltage} - \text{Second calibration resistor voltage}}{\text{Third calibration resistor impedance} - \text{Second calibration resistor impedance}} \quad (4)$$

Next, the voltage offset may be determined by subtracting the product of the excitation current and the impedance of the third calibration resistor (e.g., 244) from the voltage across the third calibration resistor (step 258):

$$\text{Voltage offset} = \text{Third calibration resistor voltage} - \text{Excitation current} * \text{Third calibration resistor impedance} \quad (5)$$

The method 250 may comprise measuring the body voltage across the body impedance (e.g., 230) (step 260) and calculating the body impedance by dividing the difference between the body voltage and the voltage offset by the excitation current (step 262):

$$\text{Body impedance} = \frac{\text{Voltage across body impedance} - \text{Voltage offset}}{\text{Excitation current}} \quad (6)$$

The method 250 may comprise calculating a first skin-electrode contact impedance by dividing the difference between the voltage across the first skin-electrode contact impedance (e.g., 226) and the voltage offset by the excitation current (step 264):

$$\text{First skin electrode contact impedance} = \frac{\text{Voltage across first skin electrode contact impedance} - \text{Voltage Offset}}{\text{Excitation current}} \quad (7)$$

The method 250 may further comprise calculating the second skin-electrode contact impedance by dividing the difference between the voltage across the second skin-electrode contact impedance (e.g., 236) and the voltage offset by the excitation current (step 266):

$$\text{Second skin electrode contact impedance} = \frac{\text{Voltage across second skin electrode contact impedance} - \text{Voltage Offset}}{\text{Excitation current}} \quad (8)$$

The method 250 also may comprise calculating an impedance variation value (IVV) by dividing the difference between the first and second calibration resistor voltages by the inter-electrode impedance (IEE) (e.g., impedance between 224 and 238) (step 268):

$$IVV = \frac{\text{Voltage across second calibration resistor} - \text{voltage across first calibration resistor}}{IEE} \quad (9)$$

where the IEE is the sum of the impedances calculated in steps 262, 264, and 266. Finally, the method 250 may comprise determining a corrected body impedance (step 270):

$$\text{Corrected body impedance} = \text{Body impedance} * \left(1 + \frac{IVV - R236}{R226 + R236}\right) \quad (10)$$

where the body impedance is the value calculated in step 262, IVV is the value determined in step 268, R236 is the second skin-electrode contact impedance 236, and R226 is the first skin-electrode contact impedance 226. The corrected body impedance may then be used as appropriate. The method 250 may be adjusted as desired, including by adding, deleting, modifying, or rearranging one or more steps. The method 250 may be performed by the processor 196, possibly in tandem with the sense electronics 237.

Figure 3A:
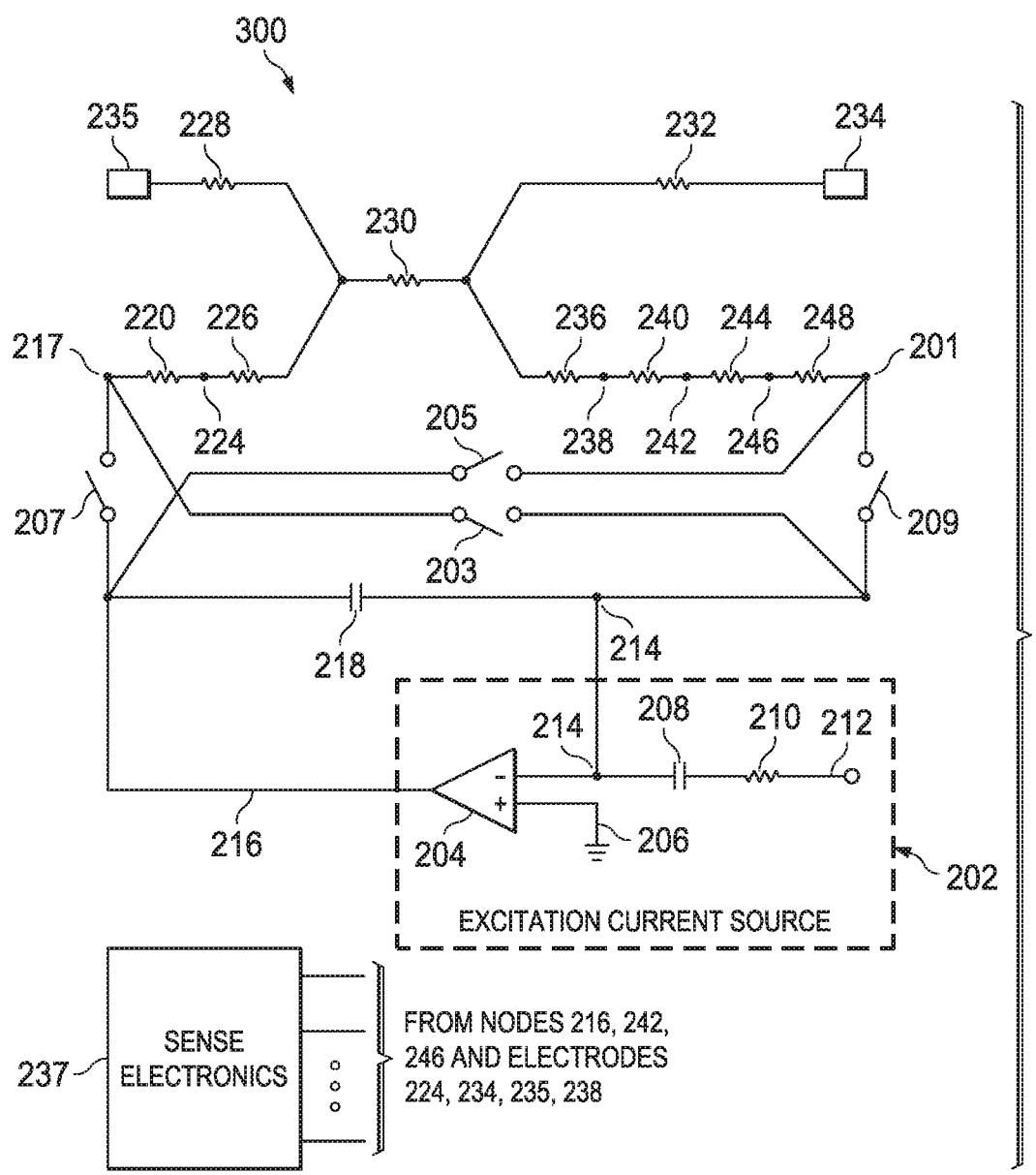
FIG. 3A is a circuit schematic diagram of another illustrative BIMCS.

FIG. 3A is a circuit schematic diagram of another illustrative BIMCS 300. The BIMCS 300 is nearly identical to the BIMCS 200, but with a few differences. Specifically, the BIMCS 300 includes a switch 203 positioned between node 217 and input 214; a switch 205 positioned between output 216 and node 201; a switch 207 positioned between the output 216 and the node 217; and a switch 209 positioned between node 201 and input 214. The switches may, for instance, be BJTs controlled by the processor 196 (FIG. 1B). The switches may be dynamically configured to reverse current flow through the calibration resistors and body impedance in the BIMCS 300.

Figure 3B:
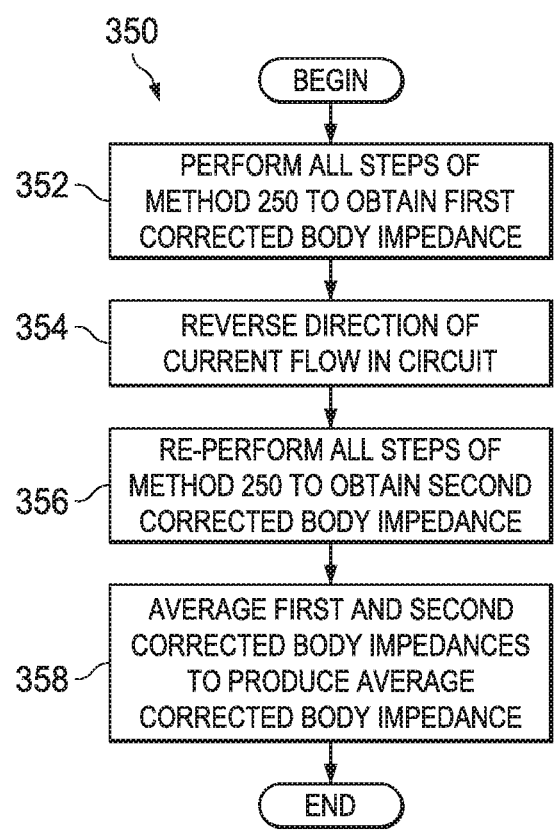
FIG. 3B is a flow diagram of an illustrative method for calibrating the illustrative BIMCS of FIG. 3A.

FIG. 3B is a flow diagram of an illustrative method 350 for calibrating the illustrative BIMCS of FIG. 3A. The method 350 is similar to the method 250 of FIG. 2B. However, the method 350 may entail performing one or more of the various measurements of the method 250 twice—once for each direction of current flow through the calibration resistors 220, 240, and 244 and body impedance 230 as determined by the configuration of switches 203, 205, 207, and 209.

The method 350 may begin by performing all steps of the method 250, described above, to obtain a first corrected body impedance (step 352). The method 350 may further comprise reversing the direction of current flow in the BIMCS 300—in particular, by adjusting switches 203, 205, 207, and 209 so that the current flow through the body impedance 230 reverses direction (step 354). The method 350 may additionally include re-performing all of the steps of the method 250 described above to obtain a second corrected body impedance (step 356). The method 350 may also comprise averaging the first and second corrected body impedances to produce an average corrected body impedance (step 358). The average corrected body impedance may then be used as desired. The method 350 may be adjusted as desired, including by adding, deleting, modifying, or rearranging one or more steps. The processor 196 may perform the method 350, possibly in tandem with the sense electronics 237.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A system, comprising:
   an excitation current source;
   a first electrode coupled to the excitation current source and associated with a first skin-electrode contact impedance;
   a second electrode coupled to the excitation current source and associated with a second skin-electrode contact impedance, the first and second electrodes configured to pass an excitation current from the excitation current source through a body;
   a first calibration resistor coupled between the excitation current source and the first electrode;
   a second calibration resistor coupled to the second electrode;
   a third calibration resistor coupled between the second calibration resistor and the excitation current source;
   a sensor configured to sense voltages across each of the first, second, and third calibration resistors; and
   a processor coupled to the sensor and configured to receive the sensed voltages, the processor further configured to:
      divide a difference in voltages across the second and third calibration resistors by a difference in impedances of the second and third calibration resistors to determine an excitation current;
      subtract a product of the excitation current and an impedance of the third calibration resistor from the voltage across the third calibration resistor to determine a voltage offset;
      measure a body voltage across two points on the body;
      divide a difference between the body voltage and the voltage offset by the excitation current to determine a body impedance;
      determine first and second skin-electrode contact impedances associated with the first and second electrodes when the first and second electrodes contact the body;
      determine an impedance variation value based on a difference between the voltages across the first and second calibration resistors and based on a total impedance between the first and second electrodes when the first and second electrodes contact the body; and
      determine a corrected body impedance based on the body impedance, the first and second skin-electrode contact impedances, and the impedance variation value.

2. The system of claim 1, wherein the total impedance comprises the body impedance and the first and second skin-electrode contact impedances.

3. The system of claim 1, wherein the processor is configured to determine the corrected body impedance based on a product of the body impedance and a sum, the sum being of 1 and a combination of the impedance variation value and the first and second skin-electrode contact impedances.

4. The system of claim 3, wherein the combination comprises a product of the impedance variation value and the second skin-electrode contact impedance divided by a sum of the first and second skin-electrode contact impedances.

5. The system of claim 1, further comprising a plurality of switches configured to reverse a direction of alternating current (AC) flowing through the first, second, and third calibration resistors, wherein the corrected body impedance accounts for parameters measured during both current flow directions.

6. The system of claim 1, further comprising a multiplexer coupled between the processor and the first and second calibration resistors.

7. A system, comprising:
   an excitation current source;
   a first electrode coupled to the excitation current source;
   a second electrode coupled to the excitation current source, the first and second electrodes configured to pass an excitation current from the excitation current source through a body;
   a first calibration resistor coupled between the excitation current source and the first electrode;
   second and third calibration resistors coupled between the excitation current source and the second electrode;
   a sensor configured to measure voltages across each of the first, second, and third calibration resistors;
   a first switch coupled between the first calibration resistor and an output of the excitation current source;
   a second switch coupled between the first calibration resistor and an input of the excitation current source;
   a third switch coupled between the third calibration resistor and the output of the excitation current source; and
   a fourth switch coupled between the third calibration resistor and the input of the excitation current source.

8. The system of claim 7, wherein the second and third calibration resistors are coupled in series with each other.

9. The system of claim 7, wherein the first calibration resistor has an impedance that is within ±15% of an impedance of the second calibration resistor.

10. The system of claim 7, wherein the excitation current source includes an amplifier that includes an inverting input coupled to the input of the excitation current source and includes an output coupled to the output of the excitation current source.

11. The system of claim 7 further comprising a processor configured to:
   set the first, second, third, and fourth switches in a first configuration to produce a first current direction through the first, second, and third calibration resistors; and
   set the first, second, third, and fourth switches in a second configuration to produce a second current direction through the first, second, and third calibration resistors that is opposite the first current direction;
   wherein the sensor is configured to measure the voltages across each of the first, second, and third calibration resistors with the first, second, third, and fourth switches in the first configuration and in the second configuration.

12. The system of claim 7 further comprising a processor configured to:
   determine a corrected body impedance associated with the first electrode and the second electrode coupled to the body based on the voltages across the first, second, and third calibration resistors.

13. The system of claim 12, wherein the processor is configured to determine the corrected body impedance by:
   determining an excitation current by dividing a difference between the voltage across the third calibration resistor and the voltage across the second calibration resistor by a difference between an impedance of the third calibration resistor and an impedance of the second calibration resistor.

14. The system of claim 13, wherein the processor is configured to determine the corrected body impedance by further:

determining a voltage offset by subtracting a product of the excitation current and the impedance of the third calibration resistor from the voltage across the third calibration resistor.

15. The system of claim 14, wherein the processor is configured to determine the corrected body impedance by further:

determining a body impedance by subtracting the voltage offset from a voltage across the body and dividing by the excitation current;

determining first and second skin electrode contact impedances; and adjusting the body impedance based on the first and second skin electrode contact impedances to determine the corrected body impedance.

16. A system comprising:

a current source that includes an input and an output;

a first electrode coupled to the current source;

a second electrode coupled to the current source, wherein the first electrode and the second electrode are configured to couple to a body such that a body impedance exists between the first electrode and the second electrode;

a first switch and a first calibration resistor coupled in series between the output of the current source and the first electrode;

a second switch coupled between the first calibration resistor and the input of the current source;

a second calibration resistor, a third calibration resistor, and a third switch coupled in series between the second electrode and the input of the current source;

a fourth switch coupled between the third calibration resistor and the output of the current source;

a sensor configured to sense voltage drops across each of the first, second, and third calibration resistors; and a processor coupled to the sensor and configured to determine the body impedance based on the voltage drops across each of the first, second, and third calibration resistors.

* * * * *